United States Patent [19]

Ishikawa et al.

[11] 4,315,982
[45] Feb. 16, 1982

[54] STYRYL PYRAZOLINE COMPOUNDS, PROCESS FOR PRODUCTION THEREOF, AND ELECTROPHOTO GRAPHIC MATERIAL COMPRISING SAID COMPOUNDS

[75] Inventors: Shozo Ishikawa, Tokyo; Shoji Masubuchi, Naka; Shigeki Ohkawa, Tokyo, all of Japan

[73] Assignee: Copyer Co., Ltd., Tokyo, Japan

[21] Appl. No.: 237,810

[22] Filed: Feb. 24, 1981

[30] Foreign Application Priority Data

Sep. 4, 1979 [JP] Japan ............................. 53-107600

[51] Int. Cl.³ .................... G03G 5/06; G03G 5/14
[52] U.S. Cl. ......................................... 430/59; 430/58; 430/76; 430/78; 542/435; 542/457; 542/458
[58] Field of Search ............... 430/58, 59, 76, 77, 430/78, 580; 542/435, 457, 458

[56] References Cited

U.S. PATENT DOCUMENTS

| 3,180,729 | 4/1965 | Klupfel et al. | 430/76 |
| 3,527,602 | 9/1970 | Fox et al. | 430/76 |
| 3,835,126 | 9/1974 | Mengler et al. | 542/458 X |
| 3,837,851 | 1/1974 | Shattuck et al. | 430/58 |
| 3,859,303 | 1/1975 | Katsuyama et al. | 430/76 X |
| 4,278,746 | 7/1981 | Goto et al. | 430/59 |

FOREIGN PATENT DOCUMENTS 1030024 5/1966 United Kingdom ................. 430/76

Primary Examiner—Roland E. Martin, Jr.
Attorney, Agent, or Firm—Sughrue, Mion, Zinn, Macpeak and Seas

[57] ABSTRACT

A compound of the formula:

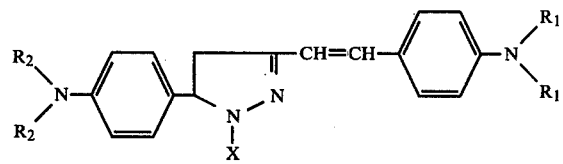

wherein $R_1$ and $R_2$ are the same or different and represent an alkyl group or combine with the nitrogen atom to form a ring, and X represents a pyridyl group, a quinolyl group, or a pyridyl or quinolyl group substituted by at least one alkyl or alkoxy group; a process for preparing the compound and an electrophotographic material containing the same.

24 Claims, 2 Drawing Figures

STYRYL PYRAZOLINE COMPOUNDS, PROCESS FOR PRODUCTION THEREOF, AND ELECTROPHOTO GRAPHIC MATERIAL COMPRISING SAID COMPOUNDS

BACKGROUND OF THE INVENTION

1. Field of the Invention

This invention relates to novel pyrazoline compounds, a process for production thereof, and an electrophotographic material comprising such a compound.

2. Description of the Prior Art

Numerous organic photoconductive substances including poly-N-vinylcarbazole have been known for use in electrophotographic materials. Photosensitive materials comprising organic photoconductive substances include the following types.

(1) A type in which a charge transfer complex is formed by a combination of an electron donor compound and an electron acceptor compound.

(2) A type in which a dye is added for sensitization.

(3) A type in which a pigment is dispersed in positive holes or electron active matrices as disclosed in U.S. Pat. No. 3,894,868 corresponding to Japanese patent application (OPI) No. 30328/72 (The term "OPI" as used herein refers to a "published unexamined Japanese patent application") (electron transport binder structures), or U.S. Pat. No. 3,870,516 corresponding to Japanese patent application (OPI) No. 18545/72 (method of imaging photoconductor in charge transport binder).

(4) A type in which the function of the photoconductor is separated into an electric charge-generating layer and a charge-transporting layer as disclosed in U.S. Pat. No. 3,837,851 corresponding to Japanese patent application (OPI) No. 105537/74 (photoconductor overcoated with triarylpyrazoline charge transport layer).

(5) Others.

The novel pyrazoline compounds of this invention can be used as a photosensitive material of any of these types, but exhibit the best characteristics when used as a charge-transporting material in a photosensitive material of the type (4) exemplified above.

U.S. Pat. No. 3,180,729 corresponding to Japanese Patent Publication No. 10366/59 (material for electrophotographic reproduction) discloses pyrazoline-type compounds, and the use of pyrazoline compounds as a charge-transporting material is disclosed in U.S. Pat. No. 3,837,851. In these prior publications, the pyrazoline compounds are limited to those in which an aryl group such as a phenyl group or a naphthyl group is located at the 1-position of the pyrazoline.

SUMMARY OF THE INVENTION

Accordingly, one object of this invention is to provide a novel pyrazoline compound which exhibits excellent characteristics when used as a charge-transporting material in an electrophotographic light-sensitive material.

Another object of this invention is to provide a process for the production of such a novel pyrazoline compound.

A further object of this invention is to provide an electrophotographic material containing the pyrazoline compound.

DETAILED DESCRIPTION OF THE INVENTION

The novel pyrazoline compound of this invention is represented by the following formula (I):

wherein $R_1$ and $R_2$ may be the same or different and represent a straight chain, branched or cyclic alkyl group such as a methyl group, an ethyl group, a propyl group or a butyl group, or $R_1$ and $R_2$ combine together with the nitrogen atom to form a ring such as a 5-membered or 6-membered ring, e.g., a morpholino ring, a piperidino ring or a pyrrolidino ring, and X represents an unsubstituted pyridyl or quinolyl group, or a pyridyl or quinolyl group substituted with at least one alkyl group which may be straight chain, branched or cyclic alkyl group such as a methyl group or an ethyl group or at least one alkoxy group such as a methoxy group or an ethoxy group as a substituent.

One method for synthesizing the novel pyrazoline compound of this invention is by refluxing a hydrazino compound of the formula (II):

wherein X represents an unsubstituted pyridyl or quinolyl group or a pyridyl or quinolyl group substituted as above, and a distyryl ketone of the formula (III):

wherein $R_1$ and $R_2$ are the same or different and represent an alkyl group such as a methyl group or an ethyl group, or combine together with the nitrogen atom to form a ring such as a morpholino ring, a piperidino ring or a pyrrolidino ring, for several hours in an alcohol together with acetic acid. Unlike synthesizing pyrazoline compounds of the formula (I) in which an aryl group is located at the 1-position in which the amount of by-products is large and the yield of the purified product is about 35% at best, a method of synthesizing pyrazoline compounds represented by the formula (I) has been found in which the pyrazolines are obtained in surprisingly high yields, after purification, of as high as about 80% based on the distyryl ketone. In this process the hydrazino compound per se or a complex salt thereof and preferably a tin complex salt thereof is reacted with the distyryl ketone of the formula (III) in dimethyl sulfoxide. The temperatures generally used for the reaction are in the range of about 60° to 110° C. for a reaction 2 to 10 hours in length. Taking the tin complex, (X-NH-NH$_2$-HCl)$_2$SnCl$_4$, where X is defined as above, a suitable molar ratio of the hydrazino compound to ketone is about 1:1 to 1.5:1.

Tin complex salts of the hydrazino compounds of the formula (II) can easily be obtained by diazotizing the corresponding amino compounds in a customary manner, and reducing the products with tin or stannous chloride and hydrochloric acid as disclosed in, for example, *J. Chem. Soc.*, 107, 691 and *J. Chem. Soc.*, 103, 1978. As an alternative method, the tin complex salts can be obtained by adding a hydrochloric acid salt of a hydrazino compound or a free hydrazino compound to a hydrochloric acid solution of stannous chloride.

The tin complex salts of the hydrazino compounds are only slightly soluble in ordinary organic solvents, but have high solubility in dimethyl sulfoxide. The high yields attained by the pyrazoline synthesizing method of this invention are believed to be due to the fact that the hydrazino compounds which are generally susceptible to oxidation and extremely unstable can be stabilized by the formation of complex salts with tin.

When the novel pyrazoline compounds of this invention are used in an electrophotographic material, the material has a much higher sensitivity than materials comprising conventional pyrazoline compounds, fluctuations in surface potential upon repeated charging and exposure can be reduced and the chargeability after high intensity exposure is rapidly restored. Such an excellent result brought about by the fact that a pyridyl or quinolyl group as opposed to a phenyl or naphthyl group is located at the 1-position in the formula (I) is quite unexpected. Of the compounds of the present invention 1-[lepidyl-(2)]-3-(p-diethylaminophenyl)-5-(p-diethylaminophenyl)pyrazoline, 1-[quinolyl-(2)]-3-(p-diethylaminophenyl)-5-(p-diethylaminophenyl)pyrazoline, 1-[pyridyl-(2)]-3-(p-diethylaminostyryl)-5-(p-diethylaminophenyl)pyrazoline and 1-[6-methoxypyridyl-(2)]-3-(p-diethylaminostyryl)-5-(p-diethylaminophenyl)pyrazoline are preferred.

The novel pyrazoline compounds of this invention show the best characteristics when used as a charge-transporting material of an electrophotographic material of type (4). Photosensitive materials of this type are described below.

When the novel pyrazoline compound of this invention is used as a charge-transporting layer, the charge-generating layer may be placed above or below the charge-transporting layer. In a photosensitive material of the type repeatedly used, it is preferred to laminate an electroconductive support, a charge-generating layer and a charge-transporting layer in this order so as to provide good physical strength.

An adhesive layer may be provided to increase adhesion between the conductive support and the charge-generating layer. Effective materials for the adhesive layer include casein and resins such as polyvinyl alcohol and watersoluble polyethylene. A suitable thickness for the adhesive layer is about 0.5 to 5 microns, preferably about 1 to 3 microns.

A vacuum-deposited layer or resin-dispersed layer of a charge-generating material such as selenium, seleniumtellurium, pyrylium, thiopyrylium-type dyes, phthalocyanine pigments, the disazo pigments disclosed in Japanese patent application (OPI) No. 37543/72 can be used as a charge-generating layer, but the present invention is not limited to combination with a specified charge-generating material. A suitable thickness for the charge-generating layer is not more than about 3 microns and preferably not more than 1 micron. A suitable thickness for the charge-transporting layer is usually about 5 to 30 microns and preferably 10 to 20 microns. These thicknesses correspond to coating amounts of about 5 to 30 g/m$^2$ and preferably about 10 to 20 g/m$^2$ as the pyrazoline compound.

The novel pyrazoline compounds of this invention are effective for transportation of positive holes. It is necessary to positively charge the photosensitive material when the charge-generating layer is located topmost. When the charge-generating layer is located between the conductive support and the charge-transporting layer, it is necessary to negatively charge the photosensitive material.

Since the novel pyrazoline compounds of this invention do not have film-forming ability, they are used in combination with a binder resin. Many resins such as acrylic resins, polystyrene, polyvinylidene chloride, polymethylmathacrylate, polyester resins and polycarbonate resins can be used as the binder resin. These binders are selected such that they are compatible with the pyrazoline compounds and the pyrazoline compounds do not crystallize when the film is dried or stored. The ability of the pyrazoline compound to transport an electric charge differs depending upon the type of the binder used. Accordingly, a binder is selected which provides the best charging characteristics, less variation in surface potential with repeated use, good insulating durability, good film strength and is not filmed by toners. Among the binder resins exemlified above, polymethylmethacrylate, polyester resins and polycarbonate are especially good.

The ratio between the novel pyrazoline compound and the binder is a balance between the physical strength and charge-transporting ability of the charge-transporting layer, is desirably such that about 0.5 to 3 parts by weight of the binder is used per part by weight of the pyrazoline compound.

In the case of a type (1) material the pyrazoline compounds of the present invention form the electron donor compound portion of a charge-transporting complex. The addition of electron acceptor compounds extends the light absorption characteristics of the pyrazoline compounds to longer wavelengths. Representative examples of the electron donor compounds used in type (1) materials are tetracyanoethylene, tetracyanoquinodinatane, chloroanil, and the like. Representative examples of the electron acceptor compounds are 2,4,7-trinitrofluorenone, 2,4,5,7-tetranitrofluorenone, nitrated dibenzotropene, nitrated dibenzothiophenesulfoxide, nitrated 9,10-phenanthrenequinone, nitrated indenothiophene, 9-dicyanomethylene-2,4,7-trinitrofluorenone, and the like. A suitable molar ratio of the electron donor compound to the electron acceptor compound is about 1:0.001 to 1:1.2.

When the charge-transporting complex is used together with a binder in a type (1) meterial, the complex is preferably used in an amount of about 50 to 90% by weight based on the total weight of the binder and complex. The binders are selected with reference to considerations similar to those acknowledged above with type (4) materials. These compositons are coated on a support and used in a manner well known to those skilled in the art.

Combinations of the electron donor and acceptor compounds suitable for a type (1) material are, for example, 1-[pyridyl-(2)]-3-(p-diethylaminostyryl)-5-(p- diethylaminophenyl)pyrazoline/2,4,7-trinitrofluorenone, 1-[quinolyl-(2)]-3-(p-diethylaminostyryl)-5-(p-diethylaminophenyl)pyrazoline/2,4,5,7-tetranitrofluorenone, and the like.

Type (2) materials combine the pyrazoline compounds of the present invention with a sensitizing dye. Representative examples of the dyes are Crystal Violet, Methyl Violet, Victory Blue, Brilliant Green, Rhodamine B, Erythrocin, Rose Bengale, Methylene Blue, pyrylium type pigments, thiopyrylium pigments, cyanine type dyestuffs and the like. The dyes are used in an amount of about 0.01 to 1% by weight based on the weight of the pyrazoline compounds. The pyrazoline will be present in the compositions in an amount of about 10 to 50% by weight based on the weight of the total amounts of the pyrazoline compounds, binder and dye, which are coated on a support in a thickness of about 5 to 30 microns to form a type (2) material. Representative combinations of sensitizing dyes and pyrazoline compounds for use in a type (2) material are, for example, 1-[pyridyl-(2)]-3-(p-diethylaminostyryl)-5-(p-diethylaminophenyl)pyrazoline/Crystal Violet, 1-[lepidyl-(2)]-3-(p-diethylaminostyryl)-5-(p-diethylaminophenyl)pyrazoline/thiacarbocyanine, and the like.

As pointed out above in a type (3) material, pigments are dispersed in positive holes or electron active matrices. These pigments are, for example, azo type pigments, phthalocyanine type pigments, bisimidazole type pigments, quinacridone tye pigments, glass fibers, selenium alloys, trigonal selenium, and the like. The electrophotographic compositions forming these type (3) materials usually will comprise about 0.1 to 10% by volume pigment, about 50 to 90% by volume of the charge-transporting material, including the pyrazoline compound of the present invention, and 10 to 50% by volume binder.

Suitable pyrazoline compound/pigment combinations for use in the present invention in a type (3) material are 1-[pyridyl-(2)]-3-(p-diethylaminostyryl)-5-(p-diethylaminophenyl)-pyrazoline/β-type copper phthalocyanine, 1-[pyridyl-(3)]-3-(p-diethylaminostyryl)-5-(p-diethylaminophenyl)pyrazoline/Cyan Blue, and the like. These combinations are combined with a binder such as an acrylic resin, a polycarbonate resin, a polyvinylidene chloride, a polyester resin, a polystyrene, or the like and coated on a conventional support in a thickness of about 5 to 30 microns.

The following Examples illustrate the present invention in more detail.

SYNTHESIS EXAMPLE 1

Synthesis of 1-[pyridyl-(2)]-3-(p-diethylaminostyryl)-5-(p-diethylaminophenyl)pyrazoline 69.00 g (0.182 mol) of di-p-diethylaminostyrylketone, 30.00 g (0.274 mol) of 2-hydrazinopyridine (the mol ratio being 1.5), 550 ml of ethanol and 91.6 ml of acetic acid were refluxed for 3.5 hours while stirring. The reaction mixture was cooled with water, and then poured into 5.5 liters of an aqueous solution containing 95 g of sodium carbonate. The resulting precipitate was separated by filtration and dried to afford 74.2 g of a yellow substance having a melting point of 80° to 110° C. The product was dissolved in 1,700 ml of cyclohexane, and hot-filtered. The filtrate was distilled under reduced pressure. The residue was hot-filtered using methanol to afford 51.30 g of a yellow substance having a melting point of 150° to 152° C. (yield 60%).

Recrystallization from acetone and methyl ethyl ketone afforded 30.05 g of a pyrazoline compound having a melting point of 153° to 154° C. (yield 35%).

Structural Formula:

Molecular Formula: $C_{30}H_{37}N_5$,
Elemental Analysis:

|  | C | H | N |
|---|---|---|---|
| Calcd. (%): | 77.05 | 7.98 | 14.98 |
| Found (%): | 77.29 | 7.98 | 15.55 |

SYNTHESIS EXAMPLE 2

Synthesis of 1-[pyridyl-(3)]-3-(p-dimethylaminostyryl)-5-(p-dimethylaminophenyl)pyrazoline

(1) 3-Hydrazinopyridine tin complex

3-Aminopyridine (28.2 g; 0.3 mol) was dissolved in 300 cc of concentrated hydrochloric acid, and was diazotized by adding a solution of 21.6 g of sodium nitrate in 180 ml of water at −5° to −1° C. Separately, stannous chloride dihydrate was dissolved in 150 ml of concentrated hydrochloric acid. The solution was cooled to −5° C. and, with strong stirring, the diazotized solution was added dropwise. About 3 hours later, the crystals that precipitated were separated by filtration and recrystallized from water to afford 62.2 g of almost colorless crystals having a melting point of 170° to 176° C. This reaction was carried out in accordance with the method of Ann., 486, 193 (1931). The structure of the 3-hydrazinopyridine tin complex was not clear.

(2) 1-[Pyridyl-(3)]-3-(p-dimethylaminostyryl)-5-(p-dimethylaminophenyl)pyrazoline Di-p-dimethylaminostyryl ketone (19.2 g; 0.06 mol), 24.9 g of the above tin complex and 120 ml of dimethyl sulfoxide were maintained at 80° C. for 3 hours with stirring, cooled with water and then poured into 1.5 liters of water. After standing overnight, a small amount of insoluble matter was removed by filtration. 60 ml of a 20% aqueous solution of sodium hydroxide was added to the filtrate (pH 3), the pH of the filtrate became 10, and a yellow precipitate formed. The precipitate was filtered, and dried to afford 25.1 g of a crude product. Recrystallization from benzene gave 19.2 g of fine needle-like crystals having a melting point of 225° to 226° C. (yield 78%).

Structural Formula:

(Py-2)

Molecular Formula: $C_{26}H_{29}N_5$
Elemental Analysis:

|  | C | H | N |
| --- | --- | --- | --- |
| Calcd. (%): | 75.88 | 7.10 | 17.02 |
| Found (%): | 75.99 | 7.16 | 17.26 |

SYNTHESIS EXAMPLE 3

Synthesis of 1-[pyridyl-(3)]-3-(p-diethylaminostyryl)-5-(p-diethylaminophenyl)pyrazoline Di-p-diethylaminostyryl ketone (7.5 g; 0.02 mol), 8.3 g of the 3-hydrazinopyridine tin complex prepared in Synthesis Example 2 and 40 ml of dimethyl sulfoxide were maintained at 80° C. for 3 hours with stirring, cooled with water, and then poured into 450 ml of water. After standing overnight, the insoluble matter was removed by filtration. 20 cc of a 20% aqueous solution of sodium hydroxide was added to the filtrate, a yellow precipitate formed and the pH of the solution became 10. The precipitate was collected by filtration and dried to afford 9.1 g of a crude product.

The crude product was boiled together with 70 ml of methanol, allowed to cool and then filtered to obtain 7.5 g of yellow crystals having a melting point of 132° to 134° C. (yield 80%).

The crystals were hot-filtered using 100 ml of acetone to remove the insoluble matter. Subsequent treatment with activated carbon afforded 5.6 g of prismatic crystals having a melting point of 133.5° to 135° C. (yield 60%).

Successive recrystallization from acetone and methyl ethyl ketone yielded crystals having a melting point of 134.5° to 136° C.
Structural Formula:

(Py-3)

Molecular Formula: $C_{30}H_{37}N_5$
Elemental Analysis:

|  | C | H | N |
| --- | --- | --- | --- |
| Calcd. (%): | 77.05 | 7.98 | 14.98 |
| Found (%): | 77.87 | 8.02 | 15.21 |

SYNTHESIS EXAMPLE 4

Synthesis of 1-[6-methoxypyridyl-(2)]-3-(p-diethylaminostyryl)-5-(p-diethylaminophenyl)pyrazoline (1) 6-Methoxy-2-hydrazinopyridine 90 g (0.626 mol) of 6-methoxy-2-chloropyridine and 313.4 g of hydrazine hydrate were refluxed for 18 hours with stirring. The reaction mixture was cooled and the oil of the bottom layer was separated. The top layer was extracted three times with diethyl ether (total volume of 450 ml). The oil and the bottom layer left after extraction with diethyl ether were distilled under reduced pressure to remove the hydrazine hydrate. The residue was dissolved in 150 ml of a 20% aqueous solution of potassium hydroxide and extracted twice with diethyl ether (total volume 300 ml). The ether extract was dried with potassium hydroxide and combined with the ether solution. The mixture was distilled to afford 22.2 g of the desired product having a boiling point of 144° to 150° C./19–20 mmHg (yield 25%). Upon cooling, the product crystallized providing crystals having a melting point of about 30° to 40° C.

(2) 1-[6-Methoxypyridyl-(2)]-3-(p-diethylaminostyryl)-5-(p-diethylaminophenyl)pyrazoline Di-p-diethylaminostyryl ketone (48.32 g; 0.128 mol), 25.0 g (0.179 mol; mol ratio 1.4) of 6-methoxy-2-hydrazinopyridine, 385 ml of ethanol and 64 ml of acetic acid were refluxed for 3 hours with stirring. The reaction mixture was cooled with water, poured into 2 l g of sodium hydroxide, 30 g of sodium carbonate and 400 ml of water, and filtered to afford a yellow brown substance having a melting point of 55° to 90° C. The product was dried and fractionally recrystallized from methanol and ethanol. Successive recrystallization from cyclohexane and acetone afforded 13.8 g of yellow crystals having a melting point of 126° to 127° C. (yield 22%).
Structural Formula:

(Py-4)

Molecular Formula: $C_{13}H_{39}N_5O$
Elemental Analysis:

|  | C | H | N |
| --- | --- | --- | --- |
| Calcd. (%): | 74.81 | 7.90 | 14.07 |
| Found (%): | 75.92 | 7.97 | 14.48 |

SYNTHESIS EXAMPLE 5

Synthesis of 1-[quinolyl-(2)]-3-(p-diethylaminostyryl)-5-(p-diethylaminophenyl)pyrazoline 2-Hydrazinoquinoline (35.70 g; 0.224 mol) obtained in a customary manner (e.g., as disclosed in *J. Chem. Soc.*, 103, 1978) from 2-chloroquinoline and hydrazine hydrate, 56.29 g (0.149 mol, mol ratio 1.5) of di-p-diethylaminostyryl ketone, 450 ml of ethanol and 74.8 ml of acetic acid were refluxed for 3 hours with stirring. The reaction mixture was cooled with water. The crystals that precipitated were separated by filtration, and hot-filtered using 150 cc of ethanol to afford 27.12 g (yield 35%) of yellow crystals having a melting point of 180° to 182° C. Recrystallization from methyl ethyl ketone afforded crystals having a melting point of 182° to 183° C.

Structural Formula:

(Py-5)

Molecular Formula: $C_{34}H_{39}N_5$
Elemental Analysis:

|  | C | H | N |
|---|---|---|---|
| Calcd. (%): | 78.88 | 7.59 | 13.53 |
| Found (%): | 78.48 | 7.29 | 13.52 |

SYNTHESIS EXAMPLE 6

Synthesis of 1-[lepidyl-(2)]-3-(p-diethylaminostyryl)-5-(p-diethylaminophenyl)pyrazoline 2-Hydrazinolepidine (37.5 g; 0.216 mol) prepared in a customary manner from 2-chlorolepidine and hydrazine hydrate, 58.23 g (0.154 mol; mol ratio 1.4) of di-p-diethylaminostyryl ketone and 463 ml of ethanol were refluxed for 3 hours with stirring. The reaction mixture was cooled with ice, and poured into 24 g of sodium hydroxide, 40.30 g of potassium carbonate and 2.5 liters of water. The precipitate that formed was filtered and dried to afford 79.2 g of a product having a melting point of 105° to 180° C. The product was fractionally recrystallized from ethanol and methanol to afford 23.5 g (yield 29%) of yellow crystals having a melting point of 182° to 184° C. Recrystallization from methyl ethyl ketone three times afforded 12.3 g of crystals having a melting point of 185.5° to 186.5° C. (yield 15%).

Structural Formula:

(Py-6)

Molecular Formula: $C_{36}H_{41}N_5$
Elemental Analysis:

|  | C | H | N |
|---|---|---|---|
| Calcd. (%): | 79.06 | 7.77 | 13.17 |
| Found (%): | 79.48 | 7.83 | 13.29 |

SYNTHESIS EXAMPLE 7

Synthesis of 1-[pyridyl-(2)]-3-(p-di-n-butylaminostyryl)-5-(p-di-n-butylaminophenyl)pyrazoline (1) 2-Hydrazinopyridine tin complex

2-Chloropyridine (390 g; 3.43 mols) and 1.6 kg (25.6 mols) of 80% hydrazine hydrate were mixed. With stirring, they were reacted for 10 hours at the refluxing temperature. The hydrazine hydrate was distilled off under reduced pressure. The undistilled portion was poured into a solution of 1.15 kg (5.1 mols) of stannous chloride in 1.5 kg (14.4 mols) of concentrated hydrochloric acid. The resulting white solid was separated by filtration, and recrystallized three times from water and once from ethanol successively to afford 1.2 kg of a 2-pyridyl hydrazine tin complex having a melting point of 86° to 89° C.

(2) Synthesis of 1-[pyridyl-(2)]-3-(p-di-n-butylaminostyryl)-5-(p-di-n-butylaminophenyl)pyrazoline A 200 ml three-necked flask was charged with 20 g (0.0409 mol) of di(p-di-n-butylaminostyryl)ketone, 25.6 g of the 2-hydradinopyridine tin complex obtained in (1) above, and 90 ml of dimethyl sulfoxide. The reaction was performed for 8.5 hours while maintaining the temperature of the solution at 90° C. The reaction mixture was allowed to stand overnight, and the precipitated yellow crystals were separated by filtration. The resulting crystals were put into water and an aqueous solution of sodium hydroxide was added to adjust the pH of the mixture to 9. The crystals were collected by filtration, washed thoroughly with water and then dried to afford 11.8 g of a yellow solid having a melting point of 101.5° to 104.5° C.

Recrystallization from methyl ethyl ketone afforded 5.5 g of yellow crystals having a melting point of 106° to 108° C. The yield of the product based on the ketone was 23%.

Structural Formula:

Molecular Formula: $C_{38}H_{53}N_5$
Elemental Analysis:

|  | C | H | N |
|---|---|---|---|
| Calcd. (%): | 78.71 | 9.21 | 12.08 |
| Found (%): | 78.76 | 9.15 | 12.03 |

SYNTHESIS EXAMPLE 8

Synthesis of 1-[pyridyl-(2)]-3-(p-N-morpholinostyryl)-5-(p-N-morpholinophenyl)pyrazoline In the same way as in Synthesis Example 7, 3.0 g of the above pyrazoline having a melting point of 202° to 203° C. was obtained by reacting 7.8 g of 2-pyridyl hydrazine tin complex and 5 g (0.0125 mol) of di(p-N-morpholinostyryl)ketone and recrystallizing the crude product from dimethylformamide. The yield was 49%.
Structural Formula:

Molecular Formula: $C_{30}H_{33}N_5O_2$
Elemental Analysis:

|  | C | H | N |
|---|---|---|---|
| Calcd. (%): | 72.70 | 6.71 | 14.13 |
| Found (%): | 72.48 | 6.47 | 14.18 |

SYNTHESIS EXAMPLE 9

Synthesis of 1-[pyridyl-(2)]-3-(p-N-piperidinostyryl)-5-(p-N-piperidinophenyl)pyrazoline In the same way as in Synthesis Example 7, 3.0 g of the above pyrazoline having a melting point of 202° to 203° C. was obtained by reacting 7.8 g of 2-pyridyl hydrazine tin complex and 5 g (0.0125 mol) of di-(p-N-piperidinostyryl)ketone, and recrystallizing the reaction mixture from dimethylformamide. The yield was 49%.
Structural Formula:

Molecular Formula: $C_{32}H_{37}N_5$
Elemental Analysis:

|  | C | H | N |
|---|---|---|---|
| Calcd. (%): | 78.17 | 7.59 | 14.24 |
| Found (%): | 78.26 | 7.43 | 14.29 |

SYNTHESIS EXAMPLE 10

Synthesis of 1-[pyridyl-(2)]-3-(p-N-pyrrolidinostyryl)-5-(p-N-pyrrolidinophenyl)pyrazoline In the same way as in Synthesis Example 7, 25.9 g (yield 70%) of the above pyrazoline having a melting point of 231° to 233° C. was obtained by reacting 37.6 g of 2-pyridyl hydrazine tin complex and 29.8 g (0.080 mol) of di-(p-N-pyrrolidinostyryl)ketone, and recrystallizing the reaction mixture successively from dimethylformamide and dimethyl sulfoxide.
Structural Formula:

Molecular Formula: $C_{30}H_{33}N_5$
Elemental Analysis:

|  | C | H | N |
|---|---|---|---|
| Calcd. (%): | 77.72 | 7.17 | 15.11 |
| Found (%): | 77.49 | 7.08 | 15.03 |

The following Examples illustrate electrophotographic materials in accordance with the present invention.

EXAMPLES 1-5

An aqueous ammonia solution of casein (11.2 g of casein, 1 g of 28% ammonia solution, and 222 g of water) was coated on an aluminum plate by a Meyer bar, and dried to form an adhesive layer at a coating amount of 1.0 g/m².

Then, 7 g of a pigment obtained by hot-filtering a β-type copper phthalocyanine (Lionol Blue NCB Toner, a product of Toyo Ink Co., Ltd.) successively with water, ethanol and benzene, 14 g of a polyester adhesive 40,000, a product of E. I. Du Pont de Nemours & Co. (solid content 20%), 35 ml of toluene and 35 ml of dioxane were charged into a ball mill, and dispersed for 6 hours. The resulting composition was coated on the aforesaid adhesive layer by a Meyer bar to form a charge-generating layer at a coating rate of 0.6 g/m² after drying.

1 g each of the pyridyl or quinolyl substituted pyrazoline compounds (Py-1, Py-3, Py-4, Py-5, Py-6) of this invention and for comparison 1-phenyl-3-(p-diethylaminostyryl)-5-(p-diethylaminophenyl)pyrazoline (Py-7) was added to a solution of 1 g of Panlite K-1300 (a polycarbonate of Teijin Chemical Co., Ltd.) in 14 ml of tetrahydrofuran to form a uniform solution. The resulting solution was coated on the aforesaid charge-generating layer to form a charge-transporting layer at a coating rate of 11 g/m².

Each of the six electrophotographic materials so produced was conditioned for 24 hours at 20° C. and a relative humidity of 65%, and corona discharged to -6 KV by a static method using Model Sp-428 (an electrostatic copying paper testing device, a product of Kawaguchi Electric Works Co., Ltd.) and maintained for 10 seconds in a dark place, and then exposed for 15 seconds to light with an illuminance of 5 lux. Thus, the charging characteristics of each of the electrophotographic materials were examined.

The initial potential $V_o$ (V), the potential retention $V_k$ (%) for 10 seconds in a dark place, the amount of exposure $E_{\frac{1}{2}}$ (lux·sec) for half decay, and the potential $V_R^{15}$ (V) of each of the photographic materials are shown in Table 1.

TABLE 1

| Example | Compound* | 1-Position | $V_o$ (-V) | $V_k$ (%) | $V_R^{15}$ (-V) | $E_{\frac{1}{2}}$ (lux·sec) |
|---|---|---|---|---|---|---|
| 1 | Py-1 | pyridin-2-yl | 335 | 52 | 0 | 3.5 |
| 2 | Py-3 | pyridin-4-yl | 420 | 62 | 10 | 5.0 |
| 3 | Py-4 | 3-methoxypyridin-2-yl | 265 | 53 | 0 | 3.0 |
| 4 | Py-5 | quinolin-2-yl | 250 | 58 | 5 | 3.0 |
| 5 | Py-6 | 4-methylquinolin-2-yl | 270 | 56 | 10 | 3.5 |
| Comparative Example 1 | Py-7 | phenyl | 550 | 68 | 0 | 8.0 |

*The pyrazoline compounds in the above table are of formula (I) in which R is an ethyl group.

It is seen from Table 1 that the pyrazoline compounds of Examples 1 to 5 have much higher sensitivity than the compound of the comparative example.

EXAMPLE 6

5 g of Diane Blue (C.I. 21180) and a solution of S-LEC BM-2 (polyvinyl butyral), a product of Sekisui Kagaku Chemical Co., Ltd. in 55 ml of ethanol were mixed and dispersed in a ball mill for 6 hours. The resulting composition was coated on the same adhesive layer as described in Examples 1 to 5 on the aluminum plate using a Meyer bar, and dried to form a charge-generating layer at a coating rate of 0.6 g/m².

1 g each of the pyrazoline compounds of this invention (Py-3) and for comparison (Py-7) was added to a solution of 1 g of Panlite K-1300 (a trademark for a polycarbonate, made by Teijin Chemical Co., Ltd.) in 14 ml of tetrahydrofuran to form a uniform solution. The solution was coated on the aforesaid charge-generating layer and dried to afford a charge-transporting layer at a coating rate of 11 g/m².

The charging characteristics measured in the same way as in Examples 1 to 5 are shown in Table 2.

TABLE 2

| Example | Compound* | 1-Position | $V_o$ (-V) | $V_k$ (%) | $V_R^{15}$ (-V) | $E_{\frac{1}{2}}$ (lux·sec) |
|---|---|---|---|---|---|---|
| 6 | Py-3 | pyridin-4-yl | 730 | 82 | 15 | 9.0 |
| Comparative Example 2 | Py-7 | phenyl | 580 | 48 | 0 | 5.0 |

*The pyrazoline compounds in the table are those of formula (I) in which R is an ethyl group.

In Example 6, the sensitivity was slightly lower than in Comparative Example 2, but the retention of the potential was much better.

EXAMPLE 7

1 g of the pyrazoline compound (Py-2) of this invention was added to a solution of Panlite K-1300 (a product of Teijin Chemical Co., Ltd.) in 30 ml of dichloromethane to form a uniform solution. The solution was coated on the same charge-generating layer as produced in Examples 1 to 5 by a Meyer bar, and dried to form a charge-transporting layer at a coating rate of 13 g/m².

The charging characteristics of the resulting material were measured in the same way as in Examples 1 to 5. The following results were obtained:

$V_o$: $-890$ V
$V_k$: 88%
$V_R^{15}$: $-50$ V
$E_{\frac{1}{2}}$: 12 lux·sec.

EXAMPLE 8

An electrophotographic material was produced by providing the same adhesive layer, charge-generating layer and charge-transporting layer as in Examples 1 to 5 on the aluminum surface of an aluminum laminated paper sheet. The material was subjected to corona discharge to $-6$ KV in an image-forming testing device (a product of Copyer Co., Ltd.) and exposed by a halogen lamp at an illuminance of 20 lux·sec. The latent image was subjected to magnetic brush development using a developer composed of an iron powder and a positively charged toner produced in a customary manner from an epoxy resin, carbon and nigrosine while applying a developing bias voltage of $-150$ V. Subsequently, the developed image was corona-transferred to a plain paper at $-5.5$ KV, and fixed by an oven heater to afford a copy free from background soiling and having good reproducibility.

EXAMPLE 9

2 g of the pyrazoline compound (Py-5) of this invention and 1 g of Panlite K-1300 (a product of Teijin Chemical Co., Ltd.) were dissolved in 14 ml of tetrahydrofuran. The solution was coated by a Meyer bar on the same adhesive layer as used in Examples 1 to 5 and formed on an aluminum plate, and dried to form a photosensitive layer at a coating rate of 11 g/m².

The charging characteristics of the photographic material obtained were measured in the same way as in Examples 1 to 5. The charge voltage was set at +6 KV.

The following results were obtained.

$V_o$: +1100 V
$V_k$: 88%
$E_{\frac{1}{2}}$: 950 lux·sec.

EXAMPLE 10

1 g of the pyrazoline compound (Py-5) of this invention, 1 g of 2,4,7-trinitrofluorene and 1 g of Panlite K-1300 (a product of Teijin Chemical Co., Ltd.) was dissolved in 14 ml of tetrahydrofuran. The solution was coated on the same adhesive layer as used in Examples 1 to 5 formed on an aluminum plate, and dried to form a photosensitive layer at a coating rate of 11 g/m².

The charging characteristics of the material were measured in the same way as in Examples 1 to 5. It was found:

$V_o$: $-255$ V
$V_k$: 68%
$E_{\frac{1}{2}}$: 420 lux·sec.

EXAMPLES 11–14

Samples were prepared in the same way as in Examples 1 to 5 using Py-8 to Py-11 instead of the pyrazolines used in Examples 1 to 5. The charging characteristics of the samples were measured under the same conditions as in Examples 1 to 5. The results are shown in Table 3.

TABLE 3

| Example | Compound | $V_o$ ($-$V) | $V_k$ (%) | $V_R^{15}$ ($-$V) | $E_{\frac{1}{2}}$ (lux · sec) |
| --- | --- | --- | --- | --- | --- |
| 11 | Py-8 | 680 | 69 | 5 | 5.7 |
| 12 | Py-9 | 540 | 65 | 0 | 5.5 |
| 13 | Py-10 | 550 | 68 | 5 | 6.1 |
| 14 | Py-11 | 440 | 64 | 0 | 4.8 |
| Comparative Example 1 | Py-7 | 550 | 68 | 0 | 8.0 |

It is seen from the results shown in Table 3 that the pyrazoline compounds of Synthesis Examples 7 to 10 have much higher sensitivity than the compound of the Comparative Example 1.

EXAMPLE 15

3 g of Diane Blue (C.I. 21180) was added to a solution of 3 g of poly(methyl methacrylate) in 60 ml of methyl ethyl ketone, and the mixture was ball-milled for 40 hours. The resulting coating composition was coated on the same undercoated aluminum plate as described in Examples 1 to 5, and dried at a coating rate of 0.3 g/m² to form a charge-generating layer. Then, a solution of 1 g of the pyrazoline compound (Py-1) of the invention and 1 g of Panlite K-1300 (polycarbonate) in 14 ml of tetrahydrofuran was coated on the charge-generating layer, and dried so that the amount of coating after drying was 11 g/m².

For comparison, a sample was prepared in the same way as above except that the pyrazoline compound (Py-7) was used instead of Py-1.

The same charge measuring device as in Examples 1 to 5 was used and variations in initial potential $V_o$ were examined by repeating charging and exposure while setting the dark decay time at 4 seconds, the illuminance at 50 lux, and the light decay time at 1 second. The results are plotted in FIG. 1. A period of 8 seconds was required for one cycle of charging and exposure.

Figure 1:
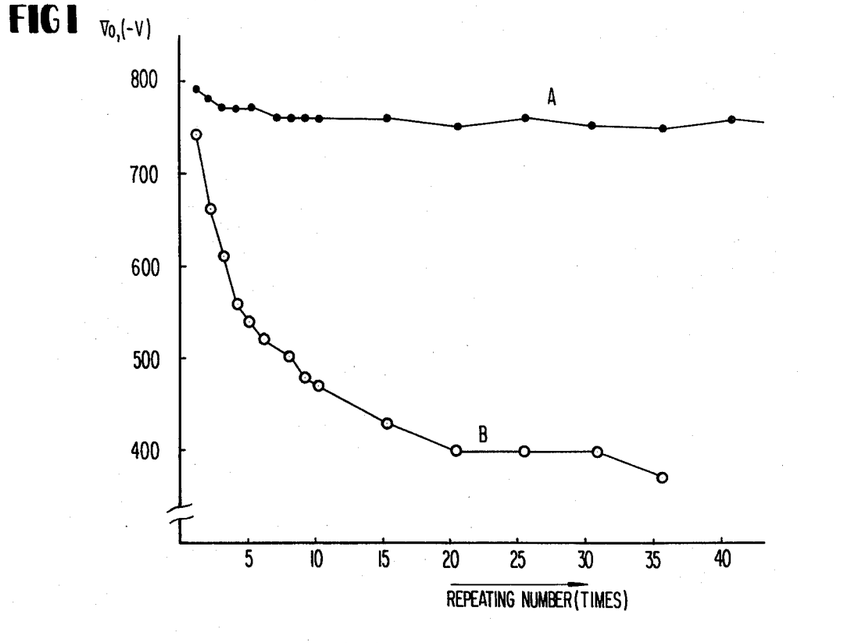
FIG. 1 is a graph showing fluctuations of Vo upon repeated charging and exposure.

In FIG. 1, curve A is for the photographic material of this example and curve B is for the comparative material. It can be seen from FIG. 1 that the pyrazoline compound of this invention has very good repeated charging characteristics. In the Comparative Experiment, the fall of initial potential due to the repetition of charging and exposure is remarkable, and this causes a marked lowering of the concentration in the continuous copying operation.

Further, in order to maintain the initial potential at the start of charging-exposure repetition, it is necessary to place the light sensitive material in the dark for a long period of time.

Thus, the repeated charging characteristics in the comparative example have serious defects in practical use, whereas the sample according to the example of the present invention has no such defects and has excellent characteristics.

Then, the sample of the present example and the sample of the comparison were each exposed to strong exposure to fluorescent lamp at 1,250 lux for 5 minutes, and then stored in the dark. Thus, ability of the charge to return to the original after strong exposure was examined. The results are shown in FIG. 2.

Figure 2:
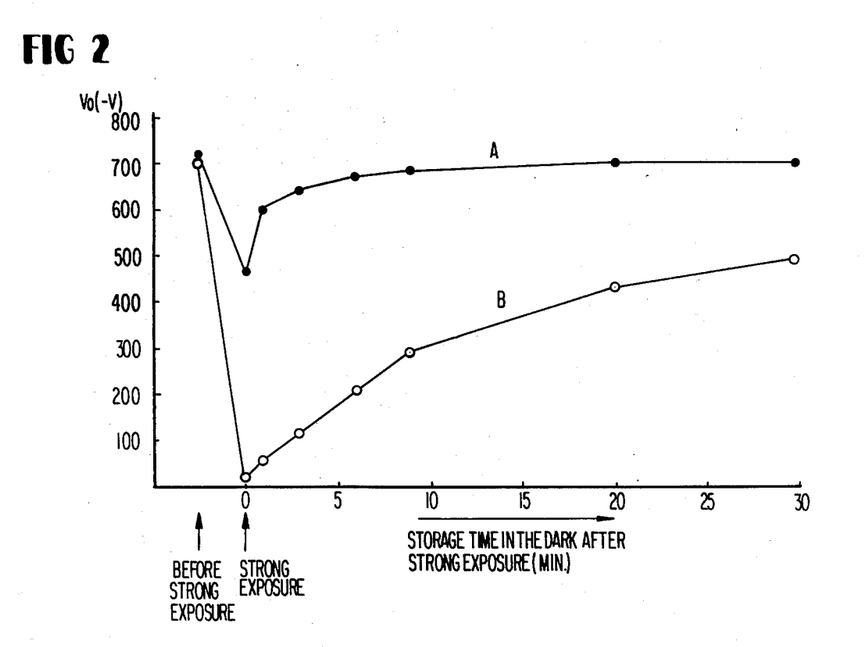
FIG. 2 is a graph showing fluctuations of Vo with the passage of time when stored in the dark after strong exposure.

In FIG. 2, curve A is for the sample of the present example and curve B is for the sample for comparison. It is seen that the sample containing the pyrazoline of this invention is less affected by strong exposure than the sample for comparison, and the returning of the charging characteristics to the original after strong exposure is very rapid.

Thus, the pyrazoline compound of this invention is much better than conventional triarylpyrazoline compounds with regard to repeated charging characteristics and the properties of charge to return to the original after strong exposure.

While the invention has been described in detail and with reference to specific embodiments thereof, it will be apparent to one skilled in the art that various changes and modifications can be made therein without departing from the spirit and scope thereof.

What is claimed is:

1. An electrophotographic material comprising a support having thereon at least one layer comprising a binder and a compound of the formula:

wherein $R_1$ and $R_2$ are the same or different and are an alkyl group or combine with the nitrogen atom to form a 5- or 6-membered ring, and X is a pyridyl group, a quinolyl group, or a pyridyl or quinolyl group substituted by at least one alkyl or alkoxy group.

2. The electrophotographic material of claim 1, wherein about 0.5 to 3 parts by weight of binder is used per part by weight of said compound.

3. The electrophotographic material of claim 2, wherein said binder is selected from the group consisting of acrylic resins, polystyrene, polyvinylidene chloride, polymethylmethacrylate, polyester resins and polycarbonate resins.

4. The electrophotographic material of claim 1, wherein said ring formed by the combination of $R_1$ and $R_2$ is a piperadino ring, a pyrrolidino ring, or a morpholino ring.

5. The electrophotographic material of claim 1, wherein X is a pyridyl group or a substituted pyridyl group.

6. The electrophotographic material of claim 1, wherein X is a quinolyl group or a substituted quinolyl group.

7. The electrophotographic material of claim 1, which comprises a support, a charge-generating layer and a separate charge-transporting layer containing said pyrazoline compound.

8. The electrophotographic material of claim 7, wherein said electrophotographic material comprises a support, a charge-generating layer and a charge-transporting layer in that order.

9. The electrophotographic material of claim 7, wherein said material comprises a support, a charge-transporting layer and charge-generating layer in that order.

10. A compound of the formula:

wherein $R_1$ and $R_2$ are the same or different and are an alkyl group or combine with the nitrogen atom to form a 5- or 6-membered ring, and X is a pyridyl group, a quinolyl group, or a pyridyl or quinolyl group substituted by at least one alkyl or alkoxy group.

11. The compound of claim 1, wherein said ring formed by the combination of $R_1$ and $R_2$ is a piperadino ring, a pyrrolidino ring, or a morpholino ring.

12. The compound of claim 1, wherein X is a pyridyl group or a substituted pyridyl group.

13. The compound of claim 1, wherein X is a quinolyl group or a substituted quinolyl group.

14. 1-[Pyridyl-(2)]-3-(p-diethylaminostyryl)-5-(p-diethylaminophenyl)pyrazoline of claim 1.

15. 1-[Pyridyl-(3)]-3-(p-diethylaminostyryl)-5-(p-diethylaminophenyl)pyrazoline of claim 1.

16. 1-[6-Methoxy-pyridyl-(2)]-3-(p-diethylaminostyryl)-5-(p-diethylaminophenyl)pyrazoline of claim 1.

17. 1-[Quinolyl-(2)]-3-(p-diethylaminostyryl)-5-(p-diethylaminophenyl)pyrazoline of claim 1.

18. 1-[Lepidyl-(2)]-3-(p-diethylaminostyryl)-5-(p-diethylaminophenyl)pyrazoline of claim 1.

19. A process for producing a pyrazoline compound of the formula:

wherein $R_1$ and $R_2$ are the same or different and are an alkyl group or combine with the nitrogen atom to form a ring, and X is a pyridyl group, a quinolyl group, or pyridyl or quinolyl group substituted by at least one alkyl or alkoxy group, which comprises reacting a tin complex salt of a hydrazino compound of the formula: $X.NH.NH_2$ wherein X is as defined above, with a distyryl ketone of the formula:

wherein $R_1$ and $R_2$ are as defined above, in dimethyl sulfoxide.

20. The compound of claim 1, wherein the at least one alkyl group which can substitute X is a methyl or ethyl group.

21. The compound of claim 1, wherein the at least one alkoxy group which can substitute X is methoxy or ethoxy.

22. The electrophotographic material of claim 11, wherein the at least one alkyl group which can substitute X is methyl or ethyl.

23. The electrophotographic material of claim 1, wherein the at least one alkoxy group which can substitute X is methoxy or ethoxy.

24. The compound of claim 1, wherein $R_1$ and $R_2$ are an alkyl group selected from the group consisting of methyl, ethyl, propyl and butyl.

* * * * *